United States Patent
Rakes et al.

(10) Patent No.: US 12,357,358 B2
(45) Date of Patent: Jul. 15, 2025

(54) PERIPROSTHETIC BONE PLATE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jordan Rakes, Cordova, TN (US); Kohsuke Watanabe, Memphis, TN (US); Adam Zysk, Germantown, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(*) Notice: Subject to any disclaimer, the term of this patent is extended or adjusted under 35 U.S.C. 154(b) by 401 days.

(21) Appl. No.: 17/921,721

(22) PCT Filed: May 17, 2021

(86) PCT No.: PCT/US2021/032709
§ 371 (c)(1),
(2) Date: Oct. 27, 2022

(87) PCT Pub. No.: WO2021/236495
PCT Pub. Date: Nov. 25, 2021

(65) Prior Publication Data
US 2023/0200871 A1    Jun. 29, 2023

Related U.S. Application Data

(60) Provisional application No. 63/027,094, filed on May 19, 2020.

(51) Int. Cl.
    *A61B 17/80* (2006.01)

(52) U.S. Cl.
    CPC ...... *A61B 17/8061* (2013.01); *A61B 17/8057* (2013.01)

(58) Field of Classification Search
    CPC .................................................. A61B 17/8061
    See application file for complete search history.

(56) References Cited

U.S. PATENT DOCUMENTS

| | | | |
|---|---|---|---|
| 3,668,692 A | 6/1972 | Englund | |
| 6,623,486 B1* | 9/2003 | Weaver | A61B 17/80 606/291 |

(Continued)

FOREIGN PATENT DOCUMENTS

| | | |
|---|---|---|
| CN | 108056808 A | 5/2018 |
| EP | 3542739 A1 | 9/2019 |

(Continued)

OTHER PUBLICATIONS

US 9,597,139 B2, 03/2017, Cavallazzi (withdrawn)

(Continued)

*Primary Examiner* — Olivia C Chang
(74) *Attorney, Agent, or Firm* — KDW Firm PLLC

(57) ABSTRACT

Periprosthetic bone plates are disclosed including, for example, a periprosthetic distal femur plate. In use, the bone plate is configured for use in periprosthetic fractures. That is, the bone plate includes one or more features to facilitate positioning and securement of the bone plate to a patient's bone that previously received a surgically implanted orthopedic implant such as, for example, an intramedullary nail, a hip prosthesis, a knee prosthesis, etc. In use, the one or more features are designed and configured to facilitate avoidance of the previous surgically implanted orthopedic implant. In addition, the bone plate is configured to facilitate percutaneous insertion of the bone plate against the patient's bone while minimizing soft tissue irritation. In addition, and/or alternatively, the bone plate is configured to provide (Continued)

improved contouring to facilitate better positioning of the bone plate against the patient's bone (e.g., better contouring adjacent patient's greater trochanter).

17 Claims, 4 Drawing Sheets

(56) References Cited

U.S. PATENT DOCUMENTS

| | | | |
|---|---|---|---|
| 7,207,993 | B1 | 4/2007 | Baldwin et al. |
| 7,341,589 | B2 | 3/2008 | Weaver et al. |
| 7,695,472 | B2 | 4/2010 | Young |
| 8,328,809 | B2 | 12/2012 | Wenk et al. |
| 8,709,092 | B2 | 4/2014 | Segina et al. |
| 8,728,168 | B2 | 5/2014 | Hanssen et al. |
| 8,808,333 | B2 | 8/2014 | Kuster et al. |
| 8,961,517 | B2 | 2/2015 | McClintock et al. |
| 9,131,968 | B2 | 9/2015 | Cavallazzi et al. |
| 9,138,244 | B2 | 9/2015 | Mebarak et al. |
| 9,138,267 | B2 | 9/2015 | Cavallazzi |
| 9,138,268 | B2 | 9/2015 | Cavallazzi et al. |
| 9,138,269 | B2 | 9/2015 | Cavallazzi et al. |
| 9,155,575 | B2 | 10/2015 | Wenk et al. |
| 9,211,151 | B2 | 12/2015 | Weaver et al. |
| 9,326,807 | B2 | 5/2016 | Schaller et al. |
| 9,345,523 | B2 | 5/2016 | Segina et al. |
| 9,463,053 | B2 | 10/2016 | Garino |
| 9,486,261 | B2 | 11/2016 | Plecko et al. |
| 9,504,503 | B2 | 11/2016 | Cavallazzi et al. |
| 9,522,066 | B2 | 12/2016 | Segina et al. |
| 9,668,794 | B2 | 6/2017 | Kuster et al. |
| 9,687,282 | B2 | 6/2017 | Strnad et al. |
| 9,707,025 | B2 | 7/2017 | Cavallazzi |
| 10,092,337 | B2 | 10/2018 | Austin et al. |
| 11,096,730 | B2 | 8/2021 | Tiongson et al. |
| 2004/0059334 | A1 | 3/2004 | Weaver et al. |
| 2004/0225291 | A1 | 11/2004 | Schwammberger et al. |
| 2008/0300637 | A1* | 12/2008 | Austin ............... A61B 17/8057 606/290 |
| 2010/0262194 | A1 | 10/2010 | Wagner et al. |
| 2012/0323284 | A1 | 12/2012 | Baker et al. |
| 2013/0013078 | A1 | 1/2013 | Hanssen et al. |
| 2013/0013080 | A1 | 1/2013 | Hanssen et al. |
| 2013/0238032 | A1 | 9/2013 | Schilter |
| 2014/0128873 | A1 | 5/2014 | McClintock et al. |
| 2014/0243907 | A1 | 8/2014 | Cavallazzi et al. |
| 2015/0051651 | A1 | 2/2015 | Terrill et al. |
| 2015/0257802 | A1 | 9/2015 | Wolf et al. |
| 2015/0282935 | A1 | 10/2015 | Kuldjanov et al. |
| 2016/0095636 | A1 | 4/2016 | Wiederkehr |
| 2016/0338748 | A1 | 11/2016 | Champagne et al. |
| 2016/0374739 | A1 | 12/2016 | Garino |
| 2017/0035476 | A1 | 2/2017 | Cavallazzi et al. |
| 2017/0056081 | A1 | 3/2017 | Langdale et al. |
| 2017/0151059 | A1 | 6/2017 | Segina et al. |
| 2018/0256220 | A1 | 9/2018 | Koay et al. |
| 2018/0256226 | A1 | 9/2018 | Govey et al. |
| 2019/0046250 | A1* | 2/2019 | Sylvestre ............. A61B 17/809 |
| 2019/0290338 | A1 | 9/2019 | Bosshard et al. |
| 2019/0365437 | A1 | 12/2019 | Leuth et al. |

FOREIGN PATENT DOCUMENTS

| | | |
|---|---|---|
| WO | 2020247381 A1 | 12/2020 |
| WO | 2021087024 A1 | 5/2021 |

OTHER PUBLICATIONS

DePuy Synthes; Periprosthetic Implants. Product Overview, dated Oct. 2013.
Fracture After Total Hip Replacement—OrthoInfo—AAOS https://orthoinfo.aaos.org/en/diseases-conditions/fractrue-after-total-hip-replacement, dated May 2018.
Zimmer; NCB® Periprosthetic Femur Plate System—Surgical Technique, dated May 2015.
International Search Report and Written Opinion for Application No. PCT/US2021/032709, mailed Sep. 6, 2021, 14 pages.

* cited by examiner

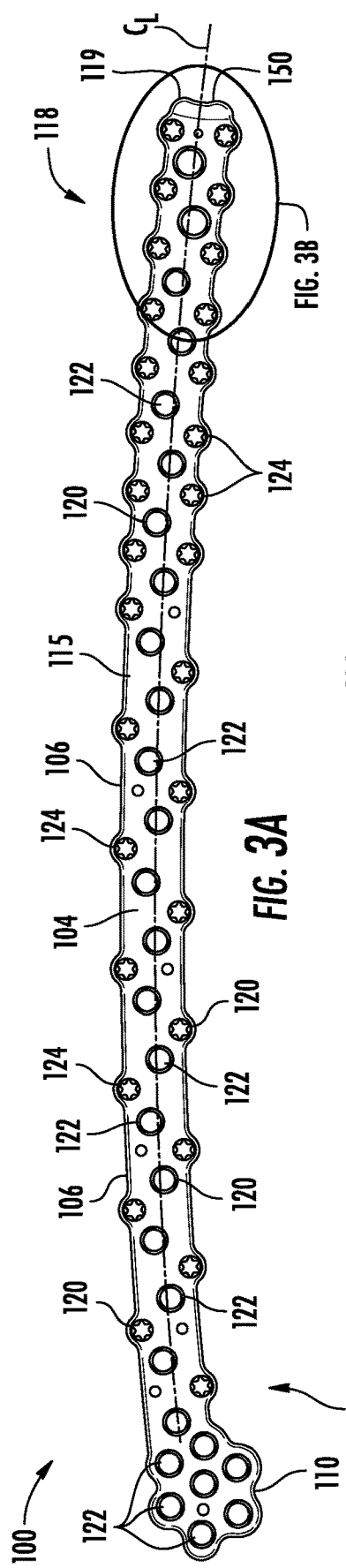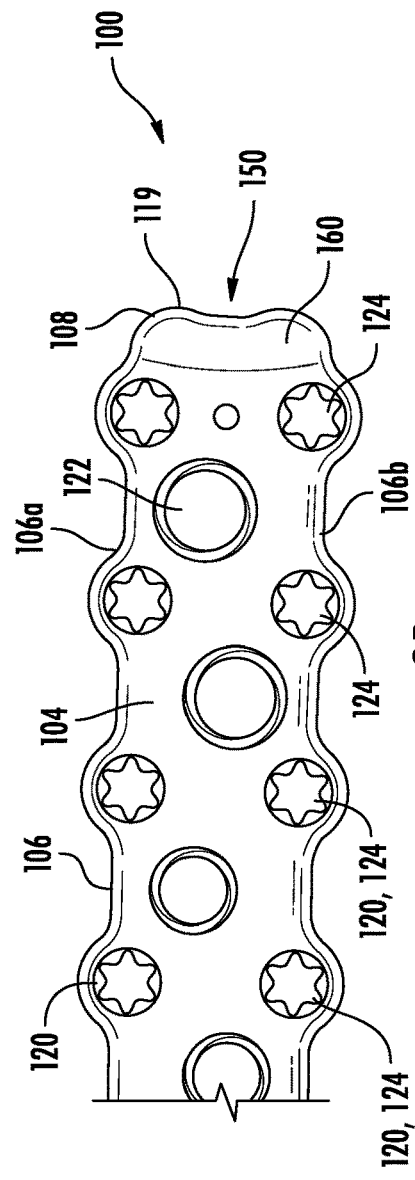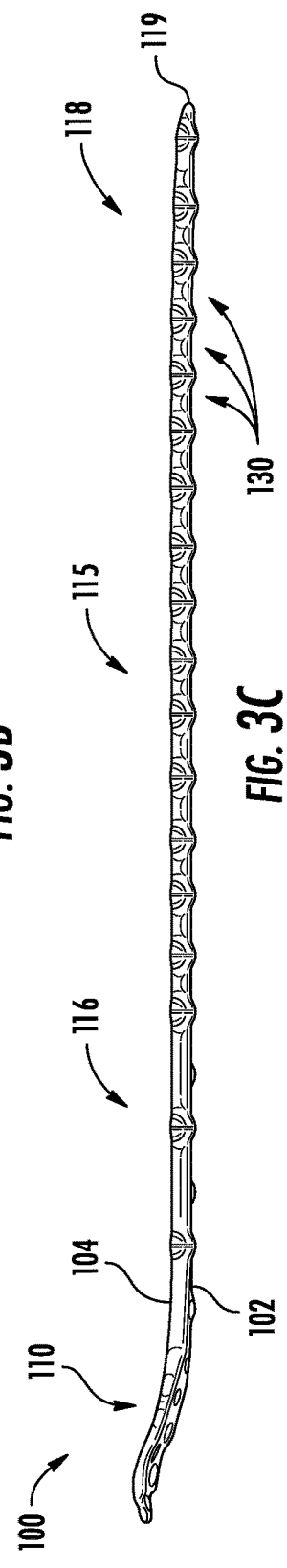
FIG. 3A
FIG. 3B
FIG. 3C

PERIPROSTHETIC BONE PLATE

CROSS-REFERENCE TO RELATED APPLICATIONS

This application is a National Phase filing of International Application No. PCT/US2021/032709, filed May 17, 2021, which application is a non-provisional of, and claims the benefit of the filing date of, U.S. provisional patent application No. 63/027,094, filed May 19, 2020, entitled "Periprosthetic Bone Plate," the entirety of each application is incorporated by reference herein.

TECHNICAL FIELD

The present disclosure is directed to orthopedic implants (e.g., bone plates) for coupling to one or more patient's bones, bone portions, bone fragments, etc., and more specifically to bone plates for facilitating stabilization of periprosthetic fractures.

BACKGROUND

Bone fractures are often repaired by securing an orthopedic implant or device to one or more patient's bone(s), bone portions, bone fragments, etc. (used interchangeably without the intent to limit). For example, it is not uncommon for a patient to receive an orthopedic knee prosthesis, an orthopedic hip prosthesis, an intramedullary ("IM") nail, etc. to repair one or more factures in a patient's bone.

On occasion a bone fracture may occur in the area surrounding a previous surgically implanted orthopedic implant or device. For example, a fracture may occur during a surgical implant procedure. Alternatively, however, as is the case in most scenarios, a periprosthetic fracture may occur in a patient years after the original surgical implant procedure. In some cases, a surgically implanted orthopedic implant may predispose a patient's bone to later fractures. In addition, it may be beneficial or necessary to secure a bone plate to a patient's bone adjacent to a surgically implanted orthopedic implant for one or more reasons.

Whatever the cause, periprosthetic fractures surrounding a previous surgically implanted orthopedic implant pose unique fixation challenges. For example, the previous surgically implanted orthopedic device or implant may interfere with the placement of a subsequently implanted orthopedic bone plate.

For example, in one scenario, a periprosthetic hip fracture may occur adjacent or around a previous surgically implanted hip replacement prosthesis or a periprosthetic knee fracture may occur adjacent or around a previous surgically implanted knee replacement prosthesis. As the number of hip and knee replacement prosthesis has increased, so too has the number of periprosthetic fractures associated therewith. Once a fracture occurs in the area surrounding a previous surgically implanted hip or knee replacement prosthesis, treatment may be complicated by osteoporosis, defects in the bone, and the presence of the previous surgically implanted hip or knee replacement prosthesis. For example, stems, rods, screws, and cement associated with the previous surgically implanted hip or knee replacement prosthesis may block the patient's medullary canal, preventing intramedullary fixation of the subsequent fracture. Moreover, stems and rods may also block screw fixation through the medullary canal to secure a subsequent bone plate to the patient's bone. As a result, periprosthetic factures and the corresponding techniques for treating periprosthetic fractures are generally more difficult, with limited options.

Nevertheless, periprosthetic fractures require treatment. For example, an unstable periprosthetic fracture may require surgical stabilization and/or implant replacement to restore function. Surgical stabilization may include implantation of a bone plate to secure the adjacent sections of the fractured bone to facilitate healing, which may occur with or without implant replacement.

Many currently known bone plates are not designed with periprosthetic fractures in mind, as a result they often exhibit one or more shortcomings or disadvantages.

In addition, coupling a bone plate to a patient's bone such as, for example, a patient's femur, introduces a number of additional challenges that need to be overcome. For example, designing, contouring, and/or bending a bone plate that approximates a patient's femur along an entire length of the patient's femur (e.g., along the femur's shaft and extending to the proximal end thereof) can be challenging. However, bending a bone plate isn't easy and can be challenging. Bone plates that are too thick can be difficult to bend. However, bone plates that are sufficiently flexible to facilitate easier bending, either pre-operative or inter-operative, may not provide adequate strength. Moreover, bending bone plates requires significant skill. For example, bending a bone plate so that it approximates the patient's bone (e.g., femur) at both ends (e.g., proximal and distal ends) of the plate is difficult.

In addition, insertion and guiding a bone plate from the distal end of the patient's femur, along the length of the femur, to a point adjacent to the proximal end of the patient's femur (e.g., adjacent to the patient's greater trochanter), all without irritation of the patient's soft tissue can be challenging. Many current bone plates are difficult to insert all the way along, for example, the patient's femur without causing significant tissue damage.

To alleviate some of these concerns, some manufacturers provide large sets or kits of bone plates to provide surgeons with different bone plate sizes and shapes. However, this has its own disadvantages due to the large number of plates needed per set, which increases costs and complexity. In addition, designing a bone plate with a screw hole pattern that is adaptable over a significant length of the plate so that a large number of bone plates isn't needed can be challenging.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an improved bone plate arranged and configured for use in periprosthetic fractures (e.g., the bone plate is arranged and configured to be coupled to a patient's bone that previously had an implant attached thereto such as, for example, a hip stem, a hip screw, a fracture plating, wires, or the like). For example, in one embodiment, the bone plate may be in the form of a distal femur plate for use in a periprosthetic fracture surrounding, for example, a hip replacement prosthesis, a knee replacement prosthesis, etc. In either event, the bone plate is designed and configured for fixation across a subsequent fracture in the patient's bone while being designed and configured with one or more features to facilitate avoidance of a previous surgically implanted orthopedic implant.

In use, the bone plate is arranged and configured to fit or be easily bent, either pre-operatively or inter-operatively, to stabilize the patient's bone such as, for example, a patient's femur.

In one embodiment, the bone plate may include a proximal end including a taper (e.g., a longitudinal taper extending from a position spaced from the end portion or leading edge of the bone plate to the end portion or leading edge of the bone plate). In use, the longitudinal taper is arranged and configured to facilitate percutaneous insertion of the bone plate against the patient's femur while minimizing soft tissue irritation. In addition, the bone plate may include a concave leading edge at the end portion of the bone plate to facilitate percutaneous insertion of the bone plate against the patient's femur while minimizing soft tissue irritation. In addition, the concave leading edge tends to keep the end portion of the bone plate (e.g., proximal end portion of the distal femur plate) centered on the patient's femur as the bone plate is advanced along the convex surface of the patient's femur and provides improved contouring to facilitate better positioning of the bone plate against the patient's bone (e.g., better contouring and/or positioning adjacent patient's greater trochanter).

In one embodiment, the end portion of the bone plate may also include a chamfer. The chamfer may include an arcuate or curved configuration substantially approximating the concave leading edge. Incorporating the chamfer and concave leading edge has been discovered to facilitate insertion of the bone plate along the patient's femur while minimizing soft tissue irritation.

In one embodiment, a periprosthetic distal femur bone plate is disclosed. The periprosthetic distal femur bone plate including a head portion and a shaft portion. The shaft portion including an upper surface, a lower surface, a central longitudinal axis, an outer periphery surface, and a proximal end positioned opposite the head portion, the proximal end defining a leading edge wherein the leading edge further comprises a concave surface defining an inwardly arcuate or curved leading surface.

In one embodiment, the shaft portion further comprises a chamfer extending from the leading edge. In one embodiment, the chamfer includes an arcuate or curved configuration approximating the inwardly arcuate or curved leading surface.

In one embodiment, the shaft portion further includes a longitudinal taper extending from the leading edge to a position X spaced from the leading edge, the longitudinal taper being arranged and configured to facilitate percutaneous insertion of the bone plate against a patient's femur.

In one embodiment, the longitudinal taper is arranged and configured to provide an increased thickness at position X and a reduced thickness at the leading edge, wherein position X is approximately 3 inches from the leading edge. In one embodiment, the increased thickness at the position X is approximately 0.225 inches and the reduced thickness at the leading edge is approximately 0.145 inches.

In one embodiment, a periprosthetic distal femur bone plate is disclosed. The periprosthetic distal femur bone plate including a head portion and a shaft portion. The shaft portion including an upper surface, a lower surface, a central longitudinal axis, an outer periphery surface, and a proximal end positioned opposite the head portion, the proximal end defining a leading edge. The shaft portion further including a longitudinal taper extending from the leading edge to a position spaced from the leading edge, the longitudinal taper being arranged and configured to facilitate percutaneous insertion of the bone plate against a patient's femur, wherein the leading edge further comprises a concave surface and a chamfer extending from the leading edge.

In one embodiment, the periprosthetic distal femur bone plate may also include a concave (e.g., bowed) bone contacting surface along a longitudinal length thereof, the concave bone contacting surface being arranged and configured to approximate the contours of the patient's femur when implanted.

In one embodiment, the periprosthetic distal femur bone plate may include adequate thickness, at least along a major length thereof, to provide improved strength.

In one embodiment, the periprosthetic distal femur bone plate may include a hole pattern arranged and configured to utilize variable angled screw holes to facilitate positioning of each bone plate over a longer length of bone.

In one embodiment, the periprosthetic distal femur bone plate may include a head portion and a shaft portion. The shaft portion including a plurality of threaded locking screw openings for securing one or more locking screws to the shaft portion of the bone plate. In addition, the shaft portion may include a plurality of variable angled fastener openings for polyaxial receiving one or more bone fasteners. In one embodiment, the variable angled fastener openings may be positioned along a periphery of the shaft portion while the locking screw openings may be centrally located (e.g., substantially adjacent a central longitudinal axis of the shaft portion).

In one embodiment, the threaded locking screw openings may be larger than the variable angled fastener openings positioned, for example, along the periphery of the shaft portion. For example, in one embodiment, the threaded locking screw openings may be sized and configured to receive, for example, 4.5 mm locking screws. The variable angled fastener openings may be sized and configured to receive, for example, 3.5 mm bone screws. Alternatively, in some embodiments, the threaded locking screw openings and the variable angled fastener openings may be the same size. For example, in some embodiments, the threaded locking screw openings and the variable angled fastener openings may be sized and configured to receive, for example, 3.5 mm bone screws.

In various embodiments, the shaft portion of the bone plate may include a first region and a second region, the first region being positioned adjacent to the head portion of the bone plate (e.g., distal portion of a distal femur plate). The first region may include non-transversely aligned variable angled fastener openings. The second region (e.g., positioned adjacent a proximal end of the patient's femur for a distal femur plate) may include variable angled fastener openings transversely aligned along the peripheral of the second region of the shaft portion (e.g., a variable angled fastener opening is positioned on either side of the central longitudinal axis transversely aligned with one another). The variable angled fastener openings in the first region alternate sides relative to one another (e.g., a single variable angled fastener opening is positioned in a row, alternating sides as one moves proximally on the shaft portion). Thus arranged, the second (proximal) region of the shaft portion includes a greater number of variable angled fastener openings to provide surgeons with increased options for placing variable angled bone fasteners.

Embodiments of the present disclosure provide numerous advantages. For example, by incorporating one or more features of the present disclosure, surgeons are provided with increased options for securing a bone plate across a subsequent fracture adjacent to a previous surgically implanted orthopedic device or implant. In addition, and/or alternatively, by incorporating one or more features of the present disclosure, the bone plates are arranged and configured to facilitate easier insertion along a patient's bone such as, for example, a patient's femur, with reduced soft tissue irritation. In addition, and/or alternatively, by incorporating one or more features of the present disclosure, the bone plates are arranged and configured to facilitate better positioning of the bone plate against the patient's bone (e.g., end portion of the bone plate may be contoured to facilitate improved placement and/or positioning adjacent patient's greater trochanter).

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 3A is a top view of an example of an embodiment of a bone plate in accordance with the present disclosure;

FIG. 3B is a detailed view of an end portion of the bone plate shown in FIG. 3A;

FIG. 3C is a side view of the bone plate shown in FIG. 3A; and

Figure 1:
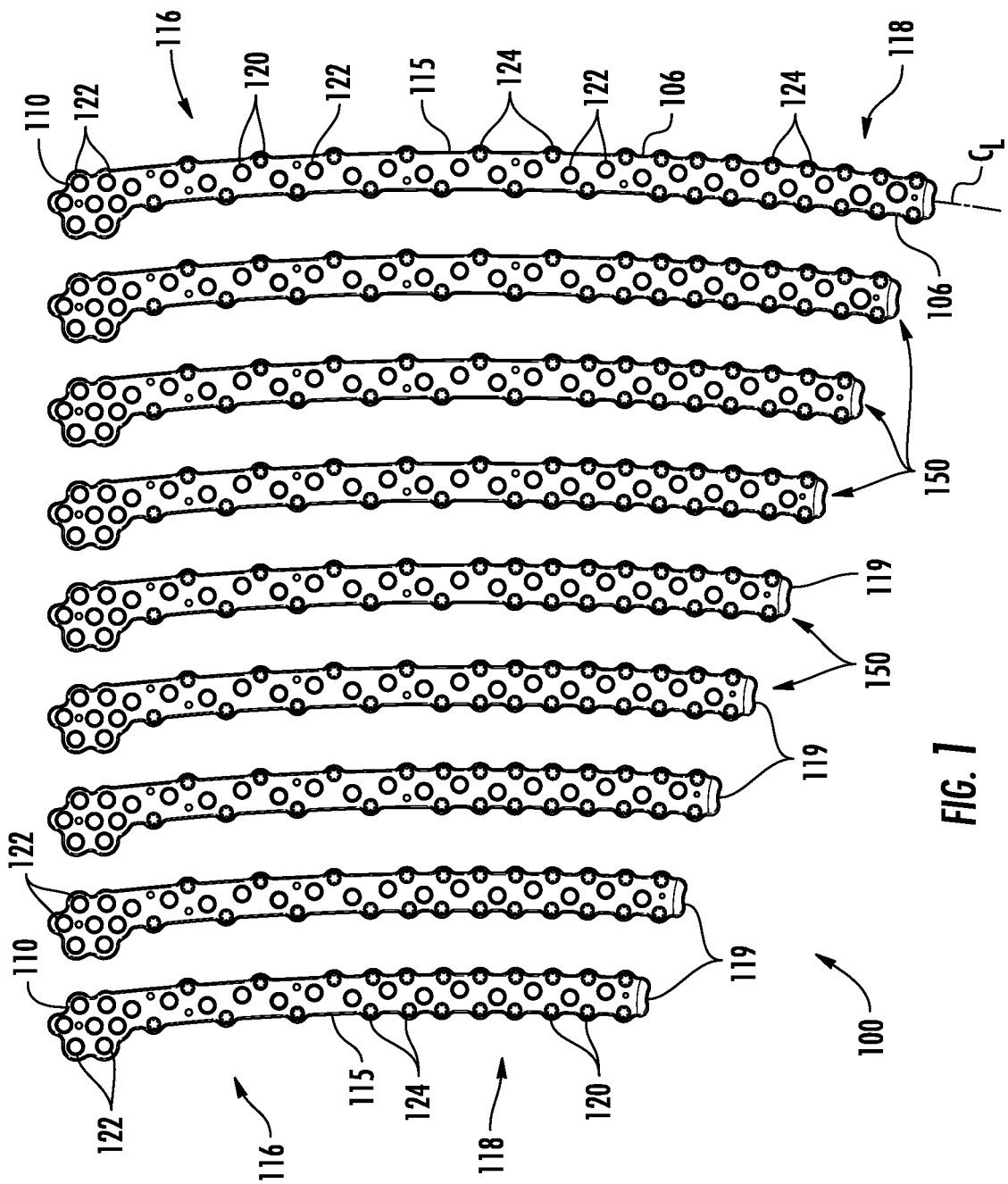
FIG. 1 is a top view of various length bone plates in accordance with the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of orthopedic bone plates will now be described more fully hereinafter with reference to the accompanying drawings, in which one or more features of the bone plates will be shown and described. It should be appreciated that the various features or the like may be used independently of, or in combination, with each other. It will be appreciated that a bone plate as disclosed herein may be embodied in many different forms and should not be construed as being limited to the embodiments set forth herein.

Rather, these embodiments are provided so that this disclosure will convey certain or features of the bone plate to those skilled in the art.

Disclosed herein are bone plates including one or more features for enabling increased flexibility for coupling the bone plates to a patient's bone adjacent to a previous surgically implanted orthopedic implant. That is, as previously mentioned and as will be appreciated by one of ordinary skill in the art, numerous patient's every year undergo surgery where one or more orthopedic devices are implanted. For example, knee replacements, hip replacement, implantation of an IM nail, etc. are commonplace. Occasionally, a bone fracture may occur in the area surrounding the surgically implanted orthopedic implant or device. These fractures are commonly referred to as periprosthetic fractures as they occur adjacent to a previous surgically implanted orthopedic device or implant.

Periprosthetic fractures pose unique fixation challenges. For example, the previous surgically implanted orthopedic device or implant may interfere with the placement and/or securement of the bone plate. For example, in one scenario, an IM nail or stem portion of the previous surgically implanted orthopedic device or implant may interfere with positioning of the bone plate and/or placement of the bone fasteners used to secure the bone plate to the patient's bone. In addition, deterioration of the patient's bone surrounding the previous surgically implanted orthopedic device or implant via, for example, osteoporosis, defects in the bone, etc. may further complicate securement and positioning of the bone plate to the patient's bone. As a result, periprosthetic factures and the corresponding techniques for treating periprosthetic fractures are generally more difficult, with limited options.

As such, as will be described herein, the present disclosure discloses a bone plate including one or more features that may be used in combination or singularly, these features are designed and configured to provide increased flexibility in enabling a surgeon to position and secure a bone plate across a fracture in a patient's bone adjacent to a previous surgically implanted orthopedic device or implant. In addition, and/or alternatively, one or more features may be provided to facilitate easier insertion of the bone plate along the patient's bone and to provide improved contouring to facilitate better positioning of the bone plate against the patient's bone (e.g., better contouring adjacent patient's greater trochanter).

As will be described herein, the bone plate may have various shapes and/or configurations. It should be appreciated that the bone plate may be provided in any suitable shape and/or configuration, which, as will be appreciated by one of ordinary skill in the art, may be dependent on the location and type of patient's bone being fixed. For example, a bone plate may include a bone conforming arcuate surface. In addition, the bone plate may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

In addition, the bone plate, may include any now known or hereafter developed additional features such as, for example, one or more openings or slots designed to receive, for example, surgical implantation tools, different fasteners (e.g., non-locking fasteners), or the like.

The bone plate may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the bone fastener may be manufactured from the same material as the bone plate. In other embodiments, the fasteners may be manufactured from a different material as compared to the bone plate.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within a locking screw opening formed in the bone plates. For example, the head portion can include threads. Alternatively, the head portion can include a series of dimples, ridges, bumps, textured areas, or any other surface that can secure the fastener.

The fastener may be any typical fastener, made out of any appropriate material. The fastener may include a bore for receiving a driver in order to drive the fastener through the bone plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the bone plate and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

In any event, as will be readily apparent from the remaining disclosure, the focus of the present disclosure is on example embodiments of bone plates including one or more features arranged and configured to provide increased flexibility for positioning and securing the bone plate adjacent to an area having a previous surgically implanted orthopedic device or implant. In addition, the bone plate may include one or more features arranged and configured to enable insertion of the bone plate against a patient's long bone (e.g., femur) while minimizing irritation of the patient's soft tissue and one or more features to provide improved contouring to facilitate better positioning of the bone plate against the patient's bone (e.g., better contouring adjacent patient's greater trochanter). Thus, it should be appreciated that the present disclosure should not be limited to any particular configuration of bone plate unless specifically claimed. In addition, while the present disclosure will be described and shown as being directed to a periprosthetic distal femur plate, it should be appreciated that features of the present disclosure have applicability and may be used in connection with other bone plates such as, for example, non-periprosthetic bone plates, humerus plates, proximal femur plates, tibia plates, etc. As such, the present disclosure should not be limited to any specific bone plate or bone plate configuration unless expressly claimed.

Referring to FIG. 1, various embodiments of a bone plate 100 having various lengths for repairing fractures in a patient's bone is disclosed. As will be described herein, the bone plates 100 may be in the form of a distal femur plate. That is, the bone plate 100 is arranged and configured for positioning adjacent to the femur of a patient. In addition, as will be described herein, the bone plate 100 includes one or more features so that the bone plate 100 facilitates positioning and securement to a patient's femur, which previously was implanted with a surgical orthopedic implant or device such as, for example, an IM nail, a hip prosthetic, a knee prosthetic, etc. As such, the bone plate 100 is arranged and configured for periprosthetic fractures and thus may be referred to as a periprosthetic bone plate or periprosthetic distal femur plate.

In addition, as will be described herein, the bone plate 100 includes one or more features so that the bone plate 100 facilitates easier insertion such as, for example, percutaneous insertion, with reduced soft tissue irritation. In addition, and/or alternatively, the bone plate 100 includes one or more features to provide improved contouring to facilitate better positioning of the bone plate against the patient's bone (e.g., better contouring adjacent patient's greater trochanter).

As will be described herein, in one or more embodiments, the bone plate 100 may include a concave cross-sectional shape along its length arranged and configured to be positioned adjacent to a patient's femur when implanted, an end portion (e.g., a proximal end portion) that is tapered (top to bottom), a concave leading edge to enhance insertion along the patient's femur, a chamfer, adequate thickness to provide adequate strength, and incorporate a hole pattern arranged and configured to receive variable angle screws that enable each bone plate to be positioned over a longer length of the patient's bone, thus reducing overall number of plates required in a set or kit.

With additional reference to FIGS. 2A-3D, as shown, the periprosthetic distal femur plate 100 may include an underside, lower, or bone facing surface 102 and an upper surface 104. In addition, the periprosthetic distal femur plate 100 includes a head portion 110 and a shaft portion 115. Moreover, the periprosthetic distal femur plate 100 includes a plurality of openings 120 formed therein for receiving a plurality of fasteners (not shown) for coupling the periprosthetic distal femur plate 100 to the patient's bone.

As will be described herein, the openings 120 may be in the form of a locking screw opening 122 or a variable angled opening 124. That is, as will be appreciated by one of ordinary skill in the art, locking screw openings 122 may include a plurality of threads formed on an inner surface thereof for mating with threads formed on an outer surface of a head portion of a bone fastener. Thus arranged, the bone fastener may be said to be locked to the periprosthetic distal femur plate 100 via the locking screw openings 122. That is, as will be appreciated by one of ordinary skill in the art, the bone fastener is threaded through one of the locking screw openings 122 formed in the periprosthetic distal femur plate 100 and into the patient's bone. The bone fastener is secured to the periprosthetic distal femur plate 100 via threads formed on the head portion of the bone fastener that cooperate with the threaded locking screw opening 122 formed in the periprosthetic distal femur plate 100. This secures the periprosthetic distal femur plate 100 with respect to the patient's bone and provides rigid fixation between the periprosthetic distal femur plate 100 and the bone fasteners. That is, because the head portion of the bone fastener interdigitates with the threads formed in the locking screw openings 122 of the periprosthetic distal femur plate 100, the plate 100 and the fasteners form a stable system or construct, and the stability of the fracture can be dependent on or aided by the stiffness of the construct. Locking a bone fastener into the periprosthetic distal femur plate 100 can achieve angular and axial stability and eliminate the possibility for the bone fastener to toggle, slide, or be dislodged, reducing the risk of postoperative loss of reduction.

As previously mentioned, the periprosthetic distal femur plate 100 also includes a plurality of variable angled openings 124 formed therein for receiving a non-locking or variable angled (e.g., polyaxial) bone fastener. In use, the variable angled openings 124 are arranged and configured to enable the bone fastener inserted therein to achieve a greater range of insertion angles as compared to, for example, a conventional locking screw that is threadably coupled to the periprosthetic distal femur plate 100. For example, in one embodiment, the angular position of the bone fastener may be rotated through a range of approximately ±15 degrees, although the range of allowable polyaxial rotation can vary, including greater and less than the fifteen degrees. In use, the variable angled openings 124 may be provided in any suitable manner, configuration, etc. now known or hereafter developed for enabling polyaxial positioning or angling of the bone fastener relative to the periprosthetic distal femur plate 100.

As shown, in one embodiment, the variable angled openings 124 may include fins or projections that extend radially inward from an inner surface of the openings 124 and into an interior region of the openings 124, and which are configured to engage or cooperate with the head portion of the bone fastener. In use, the fins engage the head portion of the bone fastener in order to secure the bone fastener at a desired position and at a desired angular orientation within the variable angled opening 124. Additional information on the operation and configuration of the fins can be found in U.S. patent application Ser. No. 15/706,877, with an earliest filing date of Jul. 25, 2005, now U.S. patent application Ser. No. 10,092,337 entitled "Systems and Methods for Using Polyaxial Plates"; U.S. patent application Ser. No. 13/524,506, filed on Jun. 15, 2012, entitled "Variable Angle Locking Implant", and International PCT Patent Application No. WO20200247381, filed on Jun. 2, 2020, entitled "Orthopedic Implant with Improved Variable Angle Locking Mechanism", the entire contents of which are hereby incorporated by reference.

In one embodiment, the locking screw openings 122 may be arranged and configured to receive larger diameter bone fasteners relative to the variable angled openings 124. That is, for example, the locking screw openings 122 may be arranged and configured to receive 4.5 mm bone fasteners while the variable angled openings 124 may be arranged and configured to receive 3.5 mm bone fasteners, although these dimensions are merely exemplary and other dimensioned bone fasteners are envisioned. By arranging and configuring the periprosthetic distal femur plate 100 to receive larger diameter locking screws, the periprosthetic distal femur plate 100 is better able to be secured to the patient's bone. Meanwhile, by incorporating smaller, variable angled openings 124, the periprosthetic distal femur plate 100 is better able to facilitate positioning of the non-locking screws around the previous surgically implanted orthopedic device or implant (e.g., smaller non-locking bone fasteners enable a surgeon to better navigate the previous surgically implanted orthopedic device or implant).

In addition, and/or alternatively, as illustrated, in one embodiment, the head portion 110 may include a plurality of locking screw openings 122, while being completely devoid of any variable angled screw openings 124 (e.g., the head portion 110 of the periprosthetic distal femur plate 100 may include exclusively locking screw openings 122), although it is envisioned that the head portion 110 may incorporate one or more variable angled openings 124.

In one embodiment, as illustrated, the shaft portion 115 of the periprosthetic distal femur plate 100 may include a plurality of locking screw openings 122 and a plurality of variable angled screw openings 124. For example, in one embodiment of the periprosthetic distal femur plate 100, the locking screw openings 122 may be more centrally located as compared to the variable angled openings 124 formed in the shaft portion 115. For example, in one embodiment, the shaft portion 115 may include a central longitudinal axis $C_L$, the locking screw openings 122 may be positioned substantially along the central longitudinal axis $C_L$ of the shaft portion 115 of the periprosthetic distal femur plate 100 while the variable angled openings 124 formed in the shaft portion 115, as illustrated, may be positioned along and/or adjacent to an outer periphery or surface 106 of the shaft portion 115 of the periprosthetic distal femur plate 100.

Thus arranged, by positioning the variable angled openings 124 along and/or adjacent to the outer periphery 106 of the shaft portion 115, the periprosthetic distal femur plate 100 is better able to position the variable angled bone fastener to avoid the previous surgically implanted orthopedic device or implant (e.g., the surgeon is better able to position and insert one or more bone fastener through the variable angled openings 124 formed in the periprosthetic distal femur plate 100 while avoiding, for example, the stem portion or IM nail of a previous surgically implanted orthopedic device or implant in the patient's femur).

In addition, and/or alternatively, as illustrated, the shaft portion 115 of the periprosthetic distal femur plate 100 may include a first region 116 and a second region 118. As illustrated, the first region 116 may be positioned adjacent to the head portion 110 of the periprosthetic distal femur plate 100 while the second region 118 may be positioned on the opposite end thereof (e.g., second region 118 may be arranged and configured to be positioned against a proximal end of the patient's femur (e.g., adjacent to the patient's trochanter)). In one or more embodiments, in the second region 118 of the shaft portion 115, the variable angled openings 124 may be arranged and configured so that they are positioned transversely to one another. That is, as illustrated, the variable angled openings 124 may be seen as being positioned in transverse rows with two variable angled openings 124 positioned in a row, one along each side or periphery surface 106 of the periprosthetic distal femur plate 100. Thus arranged, the variable angled openings 124 in the second region 118 of the shaft portion 115 may be referred to be positioned in a double row. Meanwhile, as illustrated, the variable angled openings 124 formed in the first region 116 of the shaft portion 115 of the periprosthetic distal femur plate 100 may be arranged so that they alternate relative to each other. That is, as illustrated, the variable angled openings 124 may be seen as being positioned in transverse rows with only a single variable angled opening 124 positioned in a row, with the variable angled openings 124 alternating which side or periphery surface 106 of the periprosthetic distal femur plate 100 it is positioned adjacent too. By positioning the variable angled openings 124 in double rows in the second region 118 of the shaft portion 115, the surgeon is provided with increased options when inserting variable angled bone fasteners into the patient's bone in the expected vicinity of the stem portion or IM nail of the previous surgically implanted orthopedic device or implant.

Thus arranged, the end portion 119 of the bone plate 100 may include a plurality of variable angled openings 124 (e.g., the end portion 119 may include a majority of variable angled openings 124). In use, the end portion 119 is designed to reach the proximal femur at which point the bone is no longer diaphyseal, the variable angle openings 124 allow screws to reach more desirable bone and lengths. For example, screws may target the lesser trochanter, femoral head, or some other desired region in the proximal femur. Meanwhile, by providing only a single row of alternating variable angled openings 124 in the first region 116 of the shaft portion 115, the strength of the bone plate 100 is better maintained.

While a particular bone plate configuration is shown and described, it should be appreciated that the combination of locking screw openings 122 and variable angled openings 124 may be altered in other embodiments, and the present disclosure should not be limited to any particular configuration unless expressly claimed.

In addition, and/or alternatively, the proximal end portion 119 of the bone plate 100 (e.g., end portion opposite the head portion 110) may include thinning. That is, the proximal end portion 119 may include a reduced cross-sectional area to facilitate contouring of the proximal end portion 119 relative to the patient's anatomy. Generally speaking, as will be appreciated by one of ordinary skill in the art, during use, surgeons often select a bone plate having a length sized and configured to bridge or span the entire area of the fracture. For example, it is not uncommon for a bone plate to extend from the femur condyle to the patient's trochanter or higher. In use, the head portion of the bone plate may be highly contoured to match the patient's anatomy. However, providing a bone plate with both ends contoured creates numerous issues. For example, generally speaking, providing a bone plate anatomically constrained or contoured at both ends will not fit individual patients as intended. Thus, it is beneficial to anatomically un-constrain one end of the bone plate to enable contouring of the bone plate to provide a better fit for each individual patient. In addition, and/or alternatively, providing a bone plate with both ends contoured creates numerous manufacturing issues. As such, the proximal end portion 119 (e.g., end portion opposite the head portion 110) may incorporate a reduced cross-sectional area to better enable the surgeon to contour the proximal end portion 119 to accommodate the patient's anatomy.

In addition, referring to FIGS. 2A-3D, in accordance with one or more features of the present disclosure, the bone plate 100 includes one or more features to facilitate percutaneous insertion of the bone plate 100 along the patient's bone (e.g., along the patient's femur) while minimizing soft tissue irritation. In addition, and/or alternatively, the bone plate 100 includes one or more features arranged and configured to provide improved contouring to facilitate better positioning of the bone plate 100 against the patient's bone (e.g., end portion 119 of the bone plate 100 may be contoured to facilitate improved placement and/or positioning adjacent patient's greater trochanter).

Figure 2A:
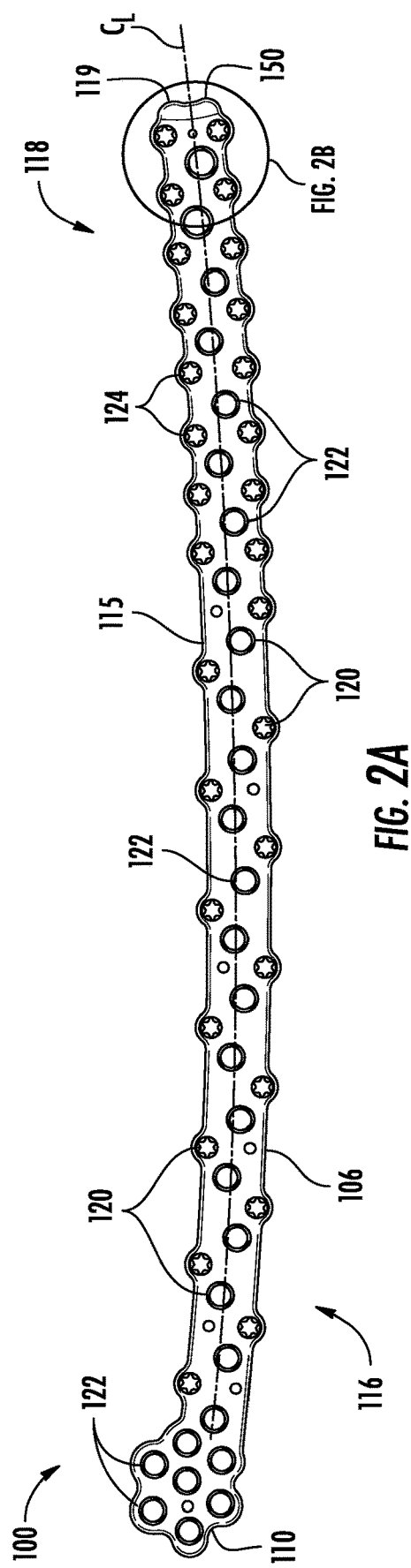
FIG. 2A is a view of an example of an embodiment of a bone plate in accordance with the present disclosure.

Referring to FIGS. 2A-3D, an example of an embodiment of a bone plate 100 in accordance with one or more features of the present disclosure, is illustrated. As illustrated in FIGS. 2A, 3A, and 3C, a full-length view of the bone plate 100 is shown. The bone plate 100 is arranged and configured to align along the patient's femur and arranged and configured to be aligned proximally near the point where the patient's greater trochanter begins to flare out from the patient's femoral shaft. FIGS. 2B and 3B shows an enlarged view of the proximal end portion 119 of the bone plate 100 (e.g., end portion arranged and configured to implanted near the patient's proximal femur).

As illustrated, in one embodiment, the bone plate 100 includes a concave leading edge 150 (e.g., an inwardly arcuate or curved surface in contrast to a straight or outwardly curved or convex surface) to facilitate insertion along the patient's femur. For example, as illustrated, the end portion 119 (e.g., proximal end portion) includes a concave leading edge 150 arranged and configured to enhance percutaneous insertion of the bone plate 100 along the patient's femur while minimizing soft tissue irritation. In use, the concave leading edge 150 acts to keep the end portion 119 of the bone plate 100 centered on the patient's femur as the bone plate 100 is advanced along the convex surface of the femur. In addition, in use, the concave leading edge 150 is arranged and configured to align the proximal end portion 119 of the bone plate 100 near the proximal portion of the patient's femur. That is, in use, the concave leading edge 150 is arranged and configured to position itself adjacent to the patient's trochanter thereby providing an improved positioning of the bone plate 100 against the patient's femur (e.g., flush against the greater trochanter).

Figure 2B:
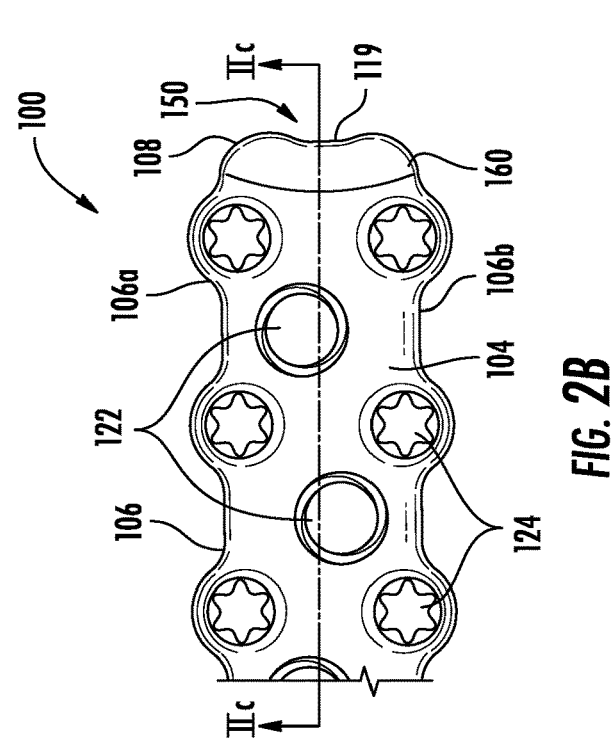
FIG. 2B is a detailed view of an end portion of the bone plate shown in FIG. 2A.

That is, as illustrated in FIGS. 2B and 3B, in one embodiment, the end portion 119 (e.g., proximal end portion) includes an underside or bone facing surface 102, an upper surface 104, first and second lateral surfaces 106a, 106b, and an end surface 108 (e.g., a leading edge). In one embodiment, the end surface 108 includes a concave or arcuate surface extending from the first and second lateral surfaces 106a, 106b to the central longitudinal axis $C_L$. By providing a concave leading edge 150, reduced soft tissue irritation is achieved during insertion of the bone plate 100 along the patient's shaft. In addition, the concave leading edge 150 tends to keep the end portion 119 of the bone plate 100 (e.g., proximal end portion of the distal femur plate 100) centered on the patient's femur as the bone plate 100 is advanced along the convex surface of the patient's femur. In addition, and/or alternatively, the concave leading edge 150 facilitates better positioning of the bone plate 100 against the patient's bone (e.g., concave leading edge 150 is contoured to facilitate improved placement and/or positioning adjacent patient's greater trochanter).

Figure 3D:
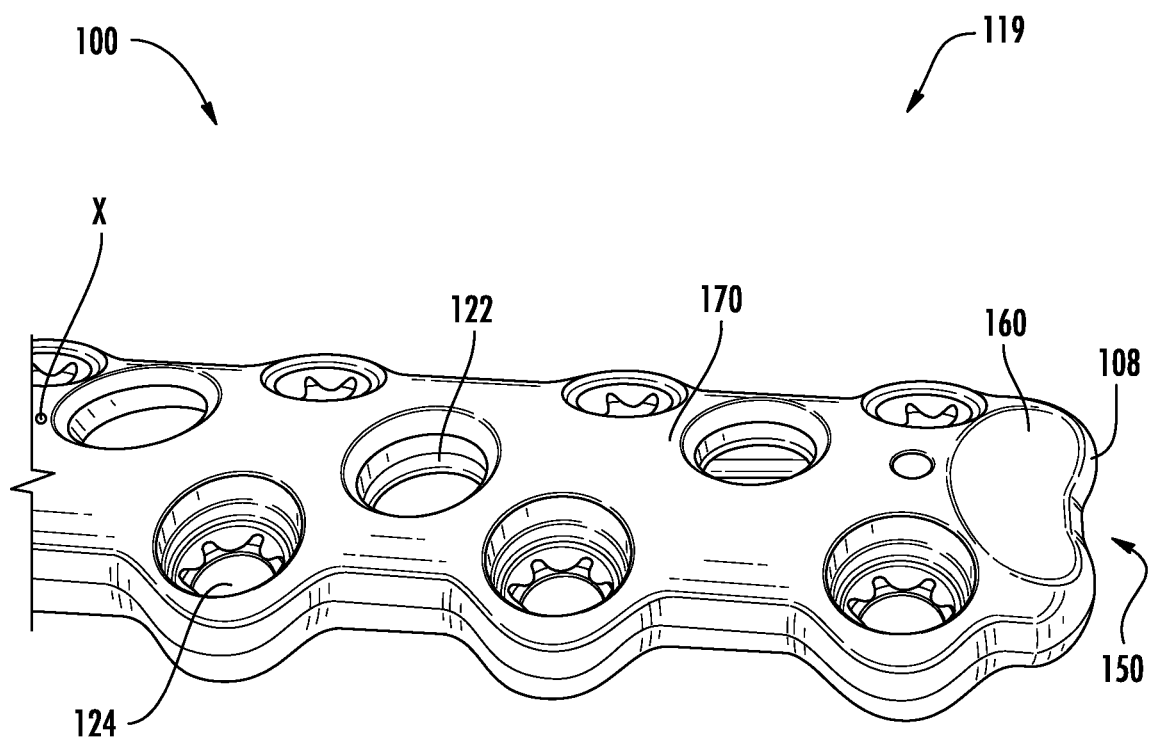
FIG. 3D is a detailed perspective view of the end portion of the bone plate shown in FIG. 3A, the end portion including a concave leading edge and a chamfer in accordance with one or more features of the present disclosure.

Referring to FIG. 3D, in addition, in accordance with one or more features of the present disclosure, the end portion 119 of the bone plate 100 may also include a chamfer 160. As illustrated, in one embodiment, when used in combination with the concave leading edge 150, the chamfer 160 may include an arcuate or curved configuration substantially approximating the concave leading edge 150. Incorporating the chamfer 160 and concave leading edge 150 has been discovered to facilitate insertion along the patient's femur while minimizing soft tissue irritation.

Figure 2C:
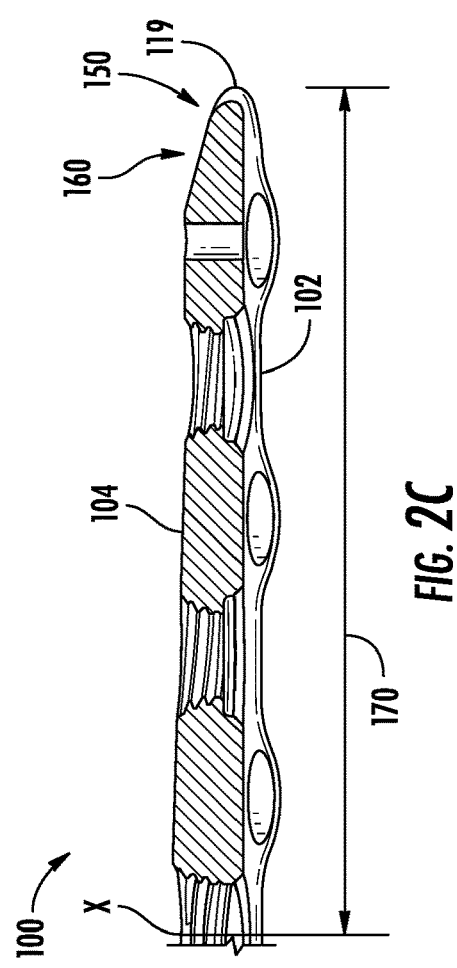
FIG. 2C is a cross-section view of the end portion of the bone plate shown in FIG. 2A, the cross-section taken along line IIC-IIC as provided in FIG. 2B.

In addition, as best illustrated in FIGS. 2C and 3D, the end portion 119 of the bone plate 100 may include a tapered top surface 170. That is, for example, starting at a position X spaced from the end surface 108 (e.g., proximal end portion)

of the bone plate 100, the shaft portion 115 may taper from an increased thickness to a reduced thickness at the end surface 108.

By providing a tapering thickness from position X to the end surface 108, easier contouring of the proximal end portion 119 of the bone plate 100 relative to the patient's anatomy is provided. That is, in accordance with one feature of the present disclosure, the proximal end portion 119 (e.g., end portion opposite the head portion 110) may incorporate a tapering or reduced cross-sectional area along a longitudinal length thereof to better enable the surgeon to contour the proximal end portion 119 to accommodate the patient's anatomy (e.g., providing the tapering end portion enables a surgeon to bend (e.g., contour) the bone plate 100 perpendicular to the bone contacting surface 102 to better contour the bone plate 100 to the patient's anatomy such as, for example patient's trochanter). That is, for example, starting at a position X spaced a distance from the end surface 108 of the bone plate 100, the shaft portion 115 may taper from an increased thickness to a reduced thickness at the end surface 108. In addition, by providing the proximal end portion of the bone plate 100 with a decreasing taper in thickness, the longitudinally tapering thickness enables easier insertion and sliding along the femur with reduced soft tissue disruption and potential damage.

In one embodiment, position X (e.g., distance at which the taper starts) may be approximately 3 inches from the end surface 108 of the bone plate 100. In addition, in one embodiment, the bone plate 100 may taper from an initial thickness of approximately 0.225 inches or 5.7 mm to a reduced thickness of 0.145 inches or 3.7 mm Although as will be appreciated by one of ordinary skill in the art, these dimensions are merely exemplary and other dimensions may be utilized.

The bone plate 100 may also include one or more additional features. For example, the bone plate 100 may include a plurality of undercuts or grooves 130 formed in the underside or bone facing surface 102. In one embodiment, the plurality of undercuts 130 may be coincidence with or collocated with the variable angled openings 124 formed in the shaft portion 115 of the bone plate 100. That is, the variable angled openings 124 formed in the shaft portion 115 may be positioned or reside within the undercuts 130 formed in the bone facing surface 102. In use, the undercuts 130 may be sized and configured to provide clearance for a cable to pass underneath the periprosthetic distal femur plate 100.

In addition, and/or alternatively, one or more of the locking screw openings 122 formed in the proximal end portion 119 of the shaft portion 115 may include an underside counterbore formed in the underside or bone facing surface 102 thereof. In use, by providing a counterbore in the underside or bone facing surface 102 of the locking screw openings 122 formed in the end portion 119 of the plate 100, the underside counterbored locking screw openings 126 may be used in combination with an instrument to grab and compress the bone fracture.

The shaft portion 115 of the bone plate 100 may also include a plurality of K-wire openings for enabling a K-wire to pass therethrough. In use, the plurality of K-wire openings allow a surgeon to provisionally hold the plate 100 to the patient's bone after they have reduced the fracture.

As generally shown in FIG. 1, and as will be appreciated by one of ordinary skill in the art, the number of undercuts, variable angled openings, locking screw openings, etc. will be variable between the various bone plates depending on the length of the plate. In addition, depending on the side of the patient's bone being coupled, the bone plate may be provided as a mirror-image of itself.

In accordance with the various features described herein, in use, a set or kit of bone plates containing a relatively reduced number of bone plates that may be implanted after one or more femoral implants is provided. In accordance with the features described herein, bone plates providing adequately rigidity or strength are disclosed while still providing sufficient flexibility to fit a patient's femur along its shaft and at the proximal end of the femur near the flare of the greater trochanter without excessive plate bending are disclosed. In addition, the insertion end (e.g., proximal end portion of a distal femur plate) of the plate is better configured to insert and guide insertion from the distal end of the patient's femur, all the way along the patient's femur, and to a point adjacent to the patient's trochanter with reduced irritation of soft tissues along the patient's femur is provided by way of, for example, top to bottom taper and side to side concave end shape. In addition, the bone plate may include a hole pattern inclusive of locking screw openings and variable angled openings providing for a reduction in the number of different plate lengths needed in a functional set.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. A periprosthetic distal femur bone plate comprising:
 a head portion; and a shaft portion including an upper surface, a lower surface, a central longitudinal axis, an outer periphery surface, and a proximal end positioned opposite the head portion, the proximal end defining a leading edge;
wherein the shaft portion includes a chamfer extending from the leading edge and the leading edge further comprises a concave surface defining an inwardly arcuate or curved leading surface, the chamfer including a concave surface mimicking the concave surface of the inwardly arcuate or curved leading surface.

2. The periprosthetic distal femur bone plate of claim 1, wherein the shaft portion further includes a longitudinal taper extending from the leading edge to a position X spaced from the leading edge, the longitudinal taper being arranged and configured to facilitate percutaneous insertion of the bone plate against a patient's femur.

3. The periprosthetic distal femur bone plate of claim 2, wherein the longitudinal taper is arranged and configured to provide an increased thickness at position X and a reduced thickness at the leading edge, wherein position X is approximately 3 inches from the leading edge.

4. The periprosthetic distal femur bone plate of claim 3, wherein the increased thickness at the position X is approximately 0.225 inches and the reduced thickness at the leading edge is approximately 0.145 inches.

5. The periprosthetic distal femur bone plate of claim 1, wherein the lower surface includes a concave bone contacting surface along a longitudinal length thereof.

6. The periprosthetic distal femur bone plate of claim 1, wherein the shaft portion further comprises:
a plurality of threaded locking screw openings arranged and configured to receive a plurality of locking screws, respectively; and
a plurality of variable angled fastener openings arranged and configured to receive a plurality of variable angled screws, respectively;
wherein the plurality of variable angled fastener openings are positioned along the outer periphery surface of the shaft portion while the plurality of locking screw openings are positioned closer to the central longitudinal axis of the shaft portion.

7. The periprosthetic distal femur bone plate of claim 6, wherein the plurality of threaded locking screw openings include a first diameter and the plurality of variable angled fastener openings include a second diameter, the first diameter being larger than the second diameter.

8. The periprosthetic bone plate of claim 1, wherein the shaft portion includes a first region and a second region, the first region being positioned adjacent to the head portion of the bone plate, the second region being positioned adjacent to the leading edge, a plurality of variable angled fastener openings formed in the first region being arranged and configured so that first and second variable angled fastener openings are non-transversely aligned, a plurality of variable angled fastener openings formed in the second region being transversely aligned in a row.

9. The periprosthetic bone plate of claim 8, wherein:
the plurality of variable angled fastener openings in the first region are arranged and configured so that a single variable angled fastener opening is positioned in a row with each row alternating sides for the variable angled fastener openings as one moves along the shaft portion; and
the plurality of variable angled fastener openings in the second region are arranged and configured so that the first and second variable angled fastener openings are positioned on either side of the central longitudinal axis transversely aligned with each other.

10. The periprosthetic bone plate of claim 8, wherein the second region of the shaft portion includes a greater number of variable angled fastener openings as compared to the first region.

11. The periprosthetic bone plate of claim 6, further comprising a plurality of undercuts formed in the lower surface of the shaft portion of the bone plate, the plurality of undercuts being coincident with the plurality of variable angled fastener openings, respectively.

12. The periprosthetic bone plate of claim 1, wherein the head portion includes a plurality of locking screw openings, while being completely devoid of any variable angled screw openings.

13. A periprosthetic distal femur bone plate comprising:
a head portion; and
a shaft portion including an upper surface, a lower surface, a central longitudinal axis, an outer periphery surface, and a proximal end positioned opposite the head portion, the proximal end defining a leading edge, the shaft portion further including:
a longitudinal taper extending from the leading edge to a position spaced from the leading edge, the longitudinal taper being arranged and configured to facilitate percutaneous insertion of the bone plate against a patient's femur;
wherein the leading edge further comprises a concave surface and a chamfer extending from the leading edge, the chamfer including a concave surface mimicking the concave surface of the leading edge.

14. A periprosthetic distal femur bone plate comprising:
a head portion; and
a shaft portion including an upper surface, a lower surface, a central longitudinal axis, an outer periphery surface, and a proximal end positioned opposite the head portion, the proximal end defining a leading edge;
wherein:
the leading edge further comprises a concave surface defining an inwardly arcuate or curved leading surface;
the shaft portion further includes a first region and a second region, the first region being positioned adjacent to the head portion of the bone plate, the second region being positioned adjacent to the leading edge, a plurality of variable angled fastener openings formed in the first region being arranged and configured so that first and second variable angled fastener openings are non-transversely aligned, a plurality of variable angled fastener openings formed in the second region being transversely aligned in a row;
the plurality of variable angled fastener openings in the first region are arranged and configured so that a single variable angled fastener opening is positioned in a row with each row alternating sides for the variable angled fastener openings as one moves along the shaft portion; and
the plurality of variable angled fastener openings in the second region are arranged and configured so that the first and second variable angled fastener openings are positioned on either side of the central longitudinal axis transversely aligned with each other.

15. The periprosthetic distal femur bone plate of claim 14, wherein the shaft portion includes a chamfer extending from the leading edge and the leading edge further comprises a concave surface defining an inwardly arcuate or curved leading surface, the chamfer including a concave surface mimicking the concave surface of the inwardly arcuate or curved leading surface.

16. A periprosthetic distal femur bone plate comprising:
   a head portion; and
   a shaft portion including an upper surface, a lower surface, a central longitudinal axis, an outer periphery surface, and a proximal end positioned opposite the head portion, the proximal end defining a leading edge;
   wherein the leading edge further comprises a concave surface defining an inwardly arcuate or curved leading surface;
   wherein the shaft portion includes a first region and a second region, the first region being positioned adjacent to the head portion of the bone plate, the second region being positioned adjacent to the leading edge, the plurality of variable angled fastener openings formed in the first region being arranged and configured so that first and second variable angled fastener openings are non-transversely aligned, the plurality of variable angled fastener openings formed in the second region being transversely aligned in a row; and
   wherein the second region of the shaft portion includes a greater number of variable angled fastener openings as compared to the first region.

17. The periprosthetic distal femur bone plate of claim 16, wherein the shaft portion includes a chamfer extending from the leading edge and the leading edge further comprises a concave surface defining an inwardly arcuate or curved leading surface, the chamfer including a concave surface mimicking the concave surface of the inwardly arcuate or curved leading surface.

* * * * *